United States Patent
Chilukuri et al.

(10) Patent No.: US 9,757,713 B2
(45) Date of Patent: Sep. 12, 2017

(54) PROCESS FOR THE PREPARATION OF 2,5-DIMETHYLEFURAN AND FURFURYL ALCOHOL OVER RUTHENIUM SUPPORTED CATALYSTS

(71) Applicant: Council of Scientific and Industrial Research, New Delhi (IN)

(72) Inventors: Satyanarayana Vera Venkata Chilukuri, Pune (IN); Atul Sopan Nagpure, Pune (IN); Nishita Satyendra Lucas, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/112,933

(22) PCT Filed: Jan. 21, 2015

(86) PCT No.: PCT/IN2015/000038
§ 371 (c)(1),
(2) Date: Jul. 20, 2016

(87) PCT Pub. No.: WO2015/111078
PCT Pub. Date: Jul. 30, 2015

(65) Prior Publication Data
US 2016/0339414 A1    Nov. 24, 2016

(30) Foreign Application Priority Data
Jan. 21, 2014    (IN) .............. 183/DEL/2014

(51) Int. Cl.
*C07D 307/02* (2006.01)
*B01J 23/63* (2006.01)
(Continued)

(52) U.S. Cl.
CPC ............ *B01J 23/63* (2013.01); *C07D 307/36* (2013.01); *C07D 307/44* (2013.01); *C07D 307/46* (2013.01); *C07D 307/48* (2013.01)

(58) Field of Classification Search
CPC ....... B01J 23/63; C07D 307/36; C07D 307/44
(Continued)

(56) References Cited

U.S. PATENT DOCUMENTS

| | | |
|---|---|---|
| 3,963,788 A | 6/1976 | Kruse et al. |
| 2008/0033188 A1 | 2/2008 | Dumesic et al. |

(Continued)

FOREIGN PATENT DOCUMENTS

WO    WO-2015/111078    7/2015

OTHER PUBLICATIONS

Julis et al, Selective hydrogenation of biomass derived substrates using ionic liquid-stabilized ruthenium nanoparticels, (Green Chem., 2010,12, p. 1634-1639.*

(Continued)

*Primary Examiner* — T. Victor Oh
(74) *Attorney, Agent, or Firm* — Schwegman Lundberg & Woessner, P.A.

(57) ABSTRACT

The present invention relates to an improved process for the preparation of 2,5-dimethylfuran and furfuryl alcohol over ruthenium supported catalysts. Further, the present invention disclosed a process for the selective hydrogenolysis of biomass derived 5-hydroxymethylfurfural (HMF) into 2,5-dimethylfuran (DMF) using Ru nanoparticles supported on NaY zeolite as a catalyst.

9 Claims, 9 Drawing Sheets

(51) Int. Cl.
C07D 307/36 (2006.01)
C07D 307/44 (2006.01)
C07D 307/46 (2006.01)
C07D 307/48 (2006.01)

(58) Field of Classification Search
USPC .......................................................... 549/503
See application file for complete search history.

(56) References Cited

U.S. PATENT DOCUMENTS

2010/0317901 A1   12/2010   Chaudhari et al.
2014/0011248 A1*  1/2014    Medoff ............... C07D 307/68
                                                        435/136

OTHER PUBLICATIONS

"International Application No. PCT/IN2015/000038, International Search Report and Written Opinion mailed Jun. 16, 2015", (Jun. 16, 2015), 9 pgs.
Alamillo, Ricardo, et al., "The selective hydrogenation of biomass-derived 5-hydroxymethylfurfural using heterogeneous catalysts", *Green Chemistry*, 14(5), (May 2012), 1413-1419.
Chen, Jiazhi, et al., "Immobilized Ru Clusters in Nanosized Mesoporous Zirconium Silica for the Aqueous Hydrogenation of Furan Derivatives at Room Temperature", *ChemCatChem*, 5(10), (2013), 2822-2826.
Chidambaram, Mandan, et al., "A two-step approach for the catalytic conversion of glucose to 2,5-dimethylfuran in ionic liquids", *Green Chemistry*, 12, (2010), 1253-1262.
Friedrich, Holger B., et al., "A study of zeolite NaY-supported ruthenate in the oxidation of alcohols", *Journal of Molecular Catalysis A: Chemical*, vol. 245, Issues 1-2,, (2006), 266-271.
Gallo, Jean Marcel R., et al., "Production and upgrading of 5-hydroxymethylfurfural using heterogeneous catalysts and biomass-derived solvents", *Green Chemistry*, 15, (2013), 85-90.
Grochowski, Matthew R., et al., "Mechanistic Study of a One-Step Catalytic Conversion of Fructose to 2,5-Dimethyltetrahydrofuran", *Chem. Eur. J.*, 18, (2012), 12363-12371.
Hansen, Thomas S., et al., "One-pot reduction of 5-hydroxymethylfurfural via hydrogen transfer from supercritical methanol", *Green Chemistry*, 14, (2012), 2457-2461.
Jae, Jungho, et al., "Production of Dimethylfuran from Hydroxymethylfurfural through Catalytic Transfer Hydrogenation with Ruthenium Supported on Carbon", *Chernsuschern*, 6(7), (2013), 1158-1162.
Liu, Huizhen, et al., "Hydrogenolysis of Glycerol to 1,2-Propanediol over Ru—Cu Bimetals Supported on Different Supports", *Clean—Soil, Air, Water*, 40(3), (Mar. 2012), 318-324.
Mishra, Dinesh K., et al., "Ruthenium nanoparticles supported on zeolite Y as an efficient catalyst for selective hydrogenation of xylose to xylitol", *Journal of Molecular Catalysis A: Chemical*, 376, (2013), 63-70.
Ordomsky, Vitaly V., et al., "Biphasic single-reactor process for dehydration of xylose and hydrogenation of produced furfural", *Applied Catalysis A: General*, 451, (2013), 6-13.
Roman-Leshkov, Yuriy, et al., "Production of dimethylfuran for liquid fuels from biomass-derived carbohydrates", *Nature*, 447, (2007), 982-985.
Thananatthanachon, Todsapon, et al., "Efficient Production of the Liquid Fuel 2,5-Dimethylfuran from Fructose Using Formic Acid as a Reagent", *Angew. Chem. Int. Ed.*, 49, (2010), 6616-6618.
Zu, Yanhong, et al., "Efficient production of the liquid fuel 2,5-dimethylfuran from 5-hydroxymethylfurfural over Ru/$Co_3O_4$ catalyst", *Applied Catalysis B: Environmental*, 146, (2014), 244-248.

* cited by examiner

PROCESS FOR THE PREPARATION OF 2,5-DIMETHYLEFURAN AND FURFURYL ALCOHOL OVER RUTHENIUM SUPPORTED CATALYSTS

PRIORITY CLAIM TO RELATED APPLICATIONS

This application is a U.S. national stage application filed under 35 U.S.C. §371 from International Application Serial No. PCT/IN2015/000038, which was filed 21 Jan. 2015, and published as WO2015/111078 on 30 Jul. 2015, and which claims priority to India Application No. 183/DEL/2014, filed 21 Jan. 2014, which applications and publication are incorporated by reference as if reproduced herein and made a part hereof in their entirety, and the benefit of priority of each of which is claimed herein.

FIELD OF THE INVENTION

The present invention relates to an improved process for the preparation of 2,5-dimethylfuran and furfuryl alcohol over ruthenium supported catalysts. Particularly, the present invention provides a process for the selective hydrogenolysis of biomass derived 5-hydroxymethylfurfural (HMF) into 2,5-dimethylfuran (DMF) using Ru nanoparticles supported on NaY zeolite as a catalyst. More particularly, the present invention provides a process for the preparation of furfuryl alcohol from furfural using Ru nanoparticles supported on NaY zeolite as a catalyst.

BACKGROUND AND PRIOR ART

Worldwide dependence on fossil reserves for the production of chemicals and fuels is alarming, as these resources are expected to exhaust gradually. Therefore, synthesis of renewable fuels from biomass has become an important area of research; to replace petroleum based fossil oils. Biomass has drawn much attention due to its potential to produce valuable organic compounds, chemicals and fuels. Hydrogenation/hydrogenolysis is an important process for the utilization of biomass, as biomass-derived materials have high oxygen content. 5-Hydroxymethylfurfural (HMF), which can be synthesized from hexoses, has been identified as a key player in the biobased renaissance, because it can be converted into levulinic acid, ethyl levulinate, γ-valerolactone, as well as the promising fuel 2,5-dimethylfuran (DMF). DMF is particularly attractive because of its superior energy density (30 kJcm$^{-3}$), high research octane number (RON=119) and nearly ideal boiling point (92-94° C.). Furthermore it is immiscible with water and is easier to blend with gasoline than ethanol. Biomass derived DMF has been successfully tested as a biofuel in a single-cylinder gasoline direct-injection (GDI) research engine. The performance of DMF was satisfactory against gasoline in terms of ignition, emission and combustion characteristics. These attributes bode well for the use of DMF as an alternative liquid fuel for transportation.

There are several recent reports in the literature on the conversion of biomass to DMF. Dumesic and co-workers utilized a two-step process to convert fructose to DMF. The first step involved the dehydration of fructose to 5-hydroxymethylfurfural (HMF) by HCl in biphasic solvent conditions followed by vapor phase hydrogenation and hydrogenolysis of HMF with a Cu—Ru/C catalyst to form DMF. Thananatthanachon and Rauchfuss provided a milder pathway for the production of DMF using formic acid as a reagent and Pd/C as catalyst. The formic acid functioned as a hydrogen donor in second step and assists the deoxygenation of HMF to DMF. For the high yield of DMF, formic acid and $H_2SO_4$ must be used. Formic acid and $H_2SO_4$ are highly corrosive and are highly harmful to humans and environment, making this process less eco-friendly. Chidambaram and Bell presented catalytic conversion of HMF to DMF with a Pd/C catalyst in ionic liquids, which gave 15% DMF yield and 47% conversion of HMF. However, a potential drawback of this method was that the solubility of hydrogen in ionic liquids is low. Hence, a high pressure of $H_2$ (62 bar) was required, which made the process energy intensive. Under similar reaction conditions, the Ru/C catalyst failed to produce DMF from HMF. Hansen et al. reported catalytic transfer hydrogenation (CTH) of HMF over Cu-containing mixed metal oxides using supercritical methanol and yielded 48% DMF. Gallo et al. studied the hydrogenolysis of HMF in the presence of lactones using a RuSn/C catalyst with a DMF yield up to 46%. Yang and Sen reported the conversion of biomass-derived carbohydrates to another promising liquid fuel 2,5-dimethyltetrahydrofuran (DMTHF) with good yield using homogeneous $RhCl_3$ and $RuCl_3$ catalysts. The same authors have also reported the synthesis of 5-methylfurfural (MF) from fructose by using heterogeneous Pd/C catalyst. Morikawa et al. studied the CTH of HMF using $AlCl_3$ and Pd/C catalysts with a DMF yield up to 60%. These CTH routes have, however, several disadvantages, as they require the use of homogeneous acid co-catalyst to enhance the hydrogenation activity and these catalysts are difficult to separate from the reaction mixture.

U.S. Pat. No. 3,963,788 discloses a process for the conversion of carbohydrates to polyhydric alcohols. Carbohydrates, such as corn starch hydrolyzate, glucose, and invert sugar, are converted to polyhydric alcohols by hydrogenation at high pressure in the presence of a ruthenium-containing alumino-silicate zeolite catalyst in which the silica/alumina mol ratio is greater than three, and in particular ruthenium on a Y type zeolite in the hydrogen form.

US20080033188 discloses a catalytic process for converting sugars to furan derivatives (e.g. 5-hydroxymethylfurfural, furfural, dimethylfuran, etc.) using a biphasic reactor containing a reactive aqueous phase and an organic extracting phase wherein the aqueous reaction solution, the organic extraction solution, or both the aqueous reaction solution and the organic extraction solution contain at least one modifier to improve selectivity of the process to yield furan derivative compound. The catalyst contains very high Ru content (10 wt %), as a part of Cu—Ru [in 3:2 ratio] catalyst supported on carbon for the hydrogenolysis of HMF to DMF. The process also requires longer reaction time (10 h) to achieve good yield of DMF (79%).

US20100317901 discloses a catalyst composition which can include: a support; a ruthenium catalyst (Ru) nanoparticle; and a linker linking the Ru nanoparticle to the support, wherein the linker is stable under hydrogenolysis conditions. The linker can include 3-aminopropyl trimethoxysilane (APTS) or derivatives thereof or such as those with amine functionality or phosphotungstic acid (PTA) or other similar solid acid agents. The support can be selected from alumina, carbon, silica, a zeolite, $TiO_2$, $ZrO_2$, or another suitable material. A specific example of a support includes zeolite, such as a NaY zeolite. The Ru nanoparticle can have a size range from about 1 nm to about 25 nm, and can be obtained by reduction of Ru salts. The novel Ru catalyst can be used for hydrogenolysis of various polyols (e.g., higher polyols) to alcohols or lower alcohols with external hydrogen being added.

Article titled "The selective hydrogenation of biomass-derived 5-hydroxymethylfurfural using heterogeneous catalysts" by R Alamillo et al. *Green Chem.*, 2012, 14, 1413-1419 reports the products produced by hydrogenation of biomass-derived 5-hydroxymethylfurfural (HMF) as potential sustainable substitutes for petroleum-based building blocks used in the production of chemicals. The hydrogenation of HMF over supported Ru, Pd, and Pt catalysts in monophasic and biphasic reactor systems is disclosed to determine the effects of the metal, support, solution phase acidity, and the solvent to elucidate the factors that determine the selectivity for hydrogenation of HMF to its fully hydrogenated form of 2,5-di-hydroxy-methyl-tetrahydrofuran (DHMTHF). The highest yields (88-91%) to DHMTHF are achieved using Ru supported on materials with high isoelectric points, such as ceria, magnesia-zirconia, and γ-alumina. Supported catalysts containing Pt and Pd at the same weight percent as Ru are not as active for the selective hydrogenation to DHMTHF.

Article titled "Hydrogenolysis of glycerol to 1,2-propanediol over Ru—Cu bimetals supported on different supports" by H Liu et al. published in *CLEAN—Soil, Air, Water, March 2012*, Volume 40 (3), pages 318-324 reports a series of Ru—Cu bimetallic catalysts were prepared using different supports in an attempt to develop highly efficient catalysts. Hydrogenolysis of aqueous solution of glycerol was performed with the supported Ru—Cu catalysts. The bimetallic catalysts were very efficient for catalyzing the hydrogenolysis of glycerol compared with the corresponding monometallic catalysts. One hundred percent of glycerol conversion and 78.5% of 1,2-propanediol yield could be achieved at 180° C. and 8 MPa.

Article titled 'Production of dimethylfuran from hydroxymethylfurfural through catalytic transfer hydrogenation with ruthenium supported on carbon" by J Jae et al. published in *Chem Sus Chem*, July 2013, Volume 6, Issue 7, pages 1158-1162 reports transfer hydrogenation using alcohols as hydrogen donors and 5 wt % Ru/C catalyst results in the selective conversion of hydroxymethylfurfural to dimethylfuran (>80% yield). During transfer hydrogenation, the hydrogen produced from alcohols is utilized in the hydrogenation of hydroxymethylfurfural. The first step is dehydration of fructose to give 5-hydroxymethyl furfural (HMF); in the second step, using copper chromite (CuCrO4) or CuRu/C catalyst HMF hydrogenolysis reaction is carried out, to give DMF; yield of DMF was 79%.

Article titled "Ruthenium nanoparticles supported on zeolite Y as an efficient catalyst for selective hydrogenation of xylose to xylitol" by D K Mishra et al. Published in *Journal of Molecular Catalysis A: Chemical*, Volume 376, September 2013, Pages 63-70 reports Zeolite Y (HYZ) supported ruthenium (Ru) nanoparticles catalysts prepared by simple impregnation method and characterized by using different techniques such as TEM, TEM-EDX, SEM, XRD, FT-IR, surface area analysis and CO chemisorption. The reaction conditions are optimized by varying the stirring rate, ruthenium percent loading, xylose concentration, hydrogen partial pressure, reaction temperature and amount of catalyst to achieve the maximum conversion of xylose and selectivity to hydrogenated product xylitol.

Article titled "Efficient production of the liquid fuel 2,5-dimethylfuran from 5-hydroxymethylfurfural over Ru/Co$_3$O$_4$ catalyst" by Y Zu et al. published in *Applied Catalysis B: Environmental*, Volume 146, March 2014, Pages 244-248, available online from Apr. 24, 2013 reports Ru/Co$_3$O$_4$ catalyst prepared by a simple co-precipitation method used to catalyze the conversion of 5-hydroxymethylfurfural (HMF) into 2,5-dimethylfuran (DMF) for the first time and exhibited excellent catalytic performance and 93.4% yield of DMF achieved at relatively low reaction temperature and H$_2$ pressure (130° C., 0.7 MPa). Higher loading of Ru (5 wt %) was used to prepare this Ru/Co$_3$O$_4$ catalyst. Moreover, longer reaction time (24 h) is needed to achieve good yield of DMF (93.4%).

Most of reported processes do not offer good space time DMF yields and are having many other drawbacks such the high metal content of the catalyst, the catalyst is not recyclable and need high H$_2$ pressure. Few processes have been reported with formic acid or 2-propanol as reducing agents, but these are either economically not feasible or commercially difficult to practice.

Therefore, there is need in the art to develop an environment friendly process for the preparation of DMF from HMF which can overcome prior art problems in terms of space time yield, recyclability, H$_2$ pressure and time.

OBJECTIVE OF INVENTION

The main objective of the present invention is to provide an improved process for the preparation of 2,5-dimethylfuran and furfuryl alcohol over ruthenium supported catalysts.

Another objective of the present invention is to provide a process for the selective hydrogenolysis of biomass derived 5-hydroxymethylfurfural (HMF) into 2,5-dimethylfuran (DMF) using Ru nanoparticles supported on NaY zeolite as a catalyst.

Another objective of the present invention is to provide a process for the preparation of furfuryl alcohol from furfural using Ru nanoparticles supported on NaY zeolite as a catalyst.

SUMMARY OF THE INVENTION

Accordingly, the present invention provides an improved process for the preparation of compound of general formula 1 wherein the said process comprising reaction of compound of general formula 2 in presence of ruthenium catalyst at 160-250° C. for 0.2-3 hours under hydrogen pressure in the range of 2-30 bar in a solvent wherein improvement is characterized in using ruthenium catalyst which comprises ruthenium nanoparticles either alone or in combination with transition metal supported on NaY zeolite.

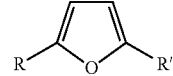

General formula 1 wherein,
R=CH$_3$ or H
R'=CH$_3$ or CH$_2$OH

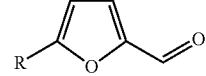

General formula 2 wherein,
R=CH$_2$OH or H

In an embodiment of the present invention transition metals are selected from Cu, Ni, Re, Cr, Mn, Fe or Co in the range of 1-10 wt % of the catalyst.

In one embodiment of the present invention ruthenium catalyst supported on NaY zeolite is selected from 2% Ru—NaY, 2% Ru—K—NaY, 2% Ru—Rb—NaY, 2% Ru—Cs—NaY, 2% Ru—Mg—NaY, 2% Ru—Ca—NaY, 2% Ru—Sr—NaY, 2% Ru—Ba—NaY, Ru—Cu [1:3]/NaY.

In another embodiment of the present invention the solvent is tetrahydrofuran.

Still in another embodiment of the present invention compounds of general formula 1 is selected from the group consisting of 2,5-dimethylfuran or furfuryl alcohol.

Still in another embodiment of the present invention compounds of general formula 2 is selected from the group consisting of 5-hydroxymethylfurfural or furfural.

Still in another embodiment of the present invention mole ratio of 5-hydroxymethylfurfural and ruthenium catalyst is in the range of 150-250.

Still, in another embodiment of the present invention conversion of compounds of general formula 2 is in the range of 90-100 mol %.

Still in another embodiment of the present invention yield of compounds of general formula 1 is in the range of 75-90 mol %.

DETAILED DESCRIPTION OF THE INVENTION

Figure 1:
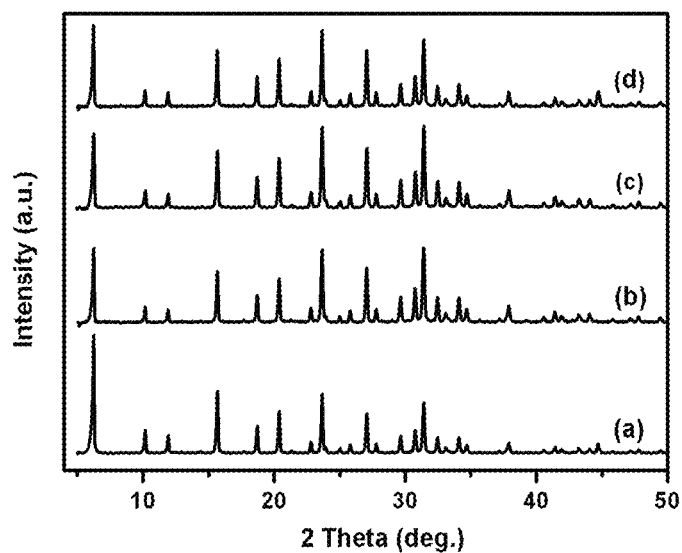
FIG. 1. XRD profiles of (a) NaY zeolite (b) 1 wt % Ru—NaY (c) 2 wt % Ru—NaY and (d) 3 wt % Ru—NaY.

The invention will now be described in detail in connection with certain preferred and optional embodiments, so that various aspects thereof may be more fully understood and appreciated.

The present invention provide a process for the selective hydrogenolysis of biomass derived 5-hydroxymethylfurfural (HMF) into 2,5-dimethylfuran (DMF) using Ru nanoparticles supported on NaY zeolite as a catalyst.

Further, the present invention provides a process for the preparation of 2,5-dimethylfuran with improved yield comprising the reaction of 5-hydroxymethylfurfural with ruthenium catalyst at 160-250° C. for 0.2-3 hours at hydrogen pressure from 2-30 bar in the presence of a solvent, wherein; said ruthenium catalyst comprises ruthenium nanoparticles either alone or in combination with transition metals supported on NaY zeolite.

The ruthenium catalyst supported on NaY zeolite is selected from 2 wt % Ru—NaY, 2 wt % Ru—K—NaY, 2 wt % Ru—Rb—NaY, 2 wt % Ru—Cs—NaY, 2 wt % Ru—Mg—NaY, 2 wt %/Ru—Ca—NaY, 2 wt % Ru—Sr—NaY, 2 wt % Ru—Ba—NaY, Ru—Cu [1:3]/NaY.

The present invention provides a process for 100% conversion of HMF with >50% selectivity to DMF, wherein said catalyst comprises 1-10 wt % metal exchanged NaY zeolite, wherein the metals are selected from noble metals and transition metals, said noble metals selected from Ru, Pt, Pd, Rh, Au, Ag, Os or Ir either alone or combination thereof in the range of 0.5-5 wt % of the catalyst, said transition metals selected from Cu, Ni, Re, Cr, Mn, Fe or Co either alone or combination thereof in the range of 1-10 wt % of the catalyst at 160-250° C., 0.2-3 hours at 2-30 bar in the presence of a solvent.

The catalysts may contain faujasite type zeolite that has an exchangeable alkali and alkaline earth metals selected from Li, Na, K, Rb, Cs, Mg, Ca, Sr or Ba either alone or combination thereof in the range of 1-10 wt % of the catalyst with noble metals and/or transition metals.

The said catalyst is recyclable at least 5 times with no appreciable loss in activity and due to its high activity and reusability it has excellent potential for the conversion of biomass into biofuels.

The solvent is selected from polar protic solvent, said polar protic solvent is preferably 2-propanol; polar aprotic solvent, said polar aprotic solvent is selected from THF (tetrahydrofuran), 1,2-DME (1,2-dimethoxyethane), $CH_3CN$ (acetonitrile) or DMSO (dimethyl sulphoxide); or non-polar solvent, said non polar solvent is preferably toluene.

EXAMPLES

The following examples are given by way of illustration of the working if the invention is actual practice and shall not be construed to limit the scope of the present invention in anyway.

Example 1

Catalyst Preparation (A) Synthesis of M-NaY Catalyst (M=Ru, Pd, Pt or Rh):

Ruthenium catalyst supported on NaY zeolite was synthesized by ion exchanged method which includes following steps. In the first step, ruthenium cations were introduced into NaY zeolite by ion-exchange method. In typical synthesis 1.96 g of NaY (CBV—100, Si/Al ratio—2.5) was dispersed in 20 mL deionized water and 8 mL $RuCl_3$ solution (Ru content 5 mg/ml, for 2 wt % Ru) and this slurry was stirred for 3 h at 80° C. temperature. The mixture was then cooled, filtered and washed until no chloride ions were detected. The remnant was dried in oven at 100° C. for 10 h. Subsequently, solid ($Ru^{+3}$/NaY) was reduced by $NaBH_4$ ($Ru/NaBH_4$=1:4 mol mol-1) in ethanol by continuous stirring at room temperature for 3 h. The sample was filtered, washed two times with 30 mL de-ionized water followed by drying in oven at 100° C. for 10 h. Similar procedure was adopted for the preparation of 1 wt % Ru—NaY and 3 wt % Ru—NaY by varying the amount of $RuCl_3$ in solution. Further, 2 wt % Pt—NaY, 2 wt % Rh—NaY and 2 wt %/Pd—NaY catalysts were also prepared by adopting similar ion exchanged process. The ruthenium, platinum, rhodium and palladium content of the samples were estimated using inductively coupled plasma optical emission spectrophotometry, ICP-OES (Spectro Arcos).

(B) Synthesis of 5 wt % Cu—NaY Catalyst:

4.75 g of NaY Zeolite (CBV—100, Si/Al ratio—2.5) was dispersed in 50 ml of distilled water along with 1.01 g of $Cu(NO_3)_2.3H_2O$ (total Cu content is 250 mg, for 5 wt % Cu loading), the above mixture was stirred for 5 h at 80° C. The sample was cooled, filtered and washed two times with deionized water and the remnant was dried in oven at 100° C. for 10 h. Solid material was calcined in air at 400° C. for 4 h followed by reduction under hydrogen atmosphere at 400° C. for 4 h.

(C) Synthesis of Ru—Cu [1:3]/NaY:

3.83 g of NaY Zeolite (CBV—100, Si/Al ratio—2.5) was dispersed in 40 ml of distilled water along with 8 ml of ruthenium chloride solution (Ru is 5 mg/ml, 40 mg of Ru metal) and 0.496 g of $Cu(NO_3)_2.3H_2O$ salt (total Cu content is 120 mg), the above mixture was stirred for 3 h at 80° C. The sample was cooled, filtered and washed until no chloride ions were detected. The wet cake was dried in oven at 100° C. for 10 h and subsequently calcined in air at 300° C. for 2 h followed by reduction under hydrogen atmosphere at 400° C. for 4 h.

(D) Synthesis of 2 wt % Ru—K—NaY:
a) Preparation of 5% K—NaY from NaY:

5 g NaY Zeolite (CBV—100, Si/Al ratio—2.5) was dispersed in 50 ml distilled water along with 1.059 g of $KNO_3$ (0.0108 moles of K) and stirred for 3 h at 80° C. The sample was then filtered, washed with deionized water and the remnant was dried in oven at 100° C. for 10 h. Solid material obtained was calcined in air at 400° C. for 4 h.
(b) Preparation of 2 wt % Ru—K—NaY from 5% K—NaY:

3.92 g 5% K—NaY was dispersed in 40 ml of distilled water along with 16 ml of $RuCl_3$ solution (Ru content is 5 mg/ml, 80 mg of Ru metal), the above mixture was stirred for 3 h at 80° C. The sample was then filtered, washed until no chloride ions were detected and the remnant was dried in oven at 100° C. for 10 h. Ion exchanged material was reduced by $NaBH_4$ (Ru/$NaBH_4$=1:4 mol $mol^{-1}$) in ethanol solution followed by drying in oven at 100° C. for 10 h. Similar procedure was adopted to prepare 2 wt % Ru—Rb—NaY from 5% Rb—NaY, 2 wt % Ru—Cs—NaY from 5% Cs—NaY, 2 wt % Ru—Ca—NaY from 5% Ca—NaY, 2 wt % Ru—Sr—NaY from 5% Sr—NaY and 2 wt % Ru—NaY from 5% Ba—NaY catalyst by ion exchange method followed by reduction in $NaBH_4$ solution at room temperature.

(E) Characterization of the catalysts:
E.1. X-Ray Diffraction

Powder diffraction patterns of different Ru metal containing NaY zeolite samples, along with parent NaY zeolite are shown in FIG. 1. The similarity in the XRD patterns of the prepared ruthenium metal exchanged samples as compared to the starting material, NaY zeolite, indicates that the zeolite structure was retained even after ion-exchange. The diffractograms show typical diffraction patterns of the faujasite framework.

E.2. BET Surface Area and $H_2$ Chemisorption

The similarity in the surface area values for the Ru exchanged NaY catalyst and the parent zeolite suggest that the NaY (Entry 1, 2, 3 and 4, Table 1) did not undergo any substantial damage during catalyst preparation method. However, there is significant decrease in the specific surface area of the catalysts as we move from 2 wt % Ru—NaY (851 $m^2/g$) to 2 wt % Ru—Cs—NaY (602 $m^2/g$). This decrease in surface area is attributed to increase in size of exchangeable alkali metal cations from $Na^+$ (102 pm) to $Cs^+$ (167 pm) ions, which is also reflected in continuous decrease in pore volume. Metal dispersion values were obtained by a $H_2$ chemisorption method. The dispersion values (%) for the Ru exchanged NaY samples (Entry 2, 3 and 4, Table 1) are: 1 wt % Ru—NaY, 47.4%; 2 wt % Ru—NaY, 53.2% and 3 wt % Ru—NaY, 19.3%. The higher Ru metal dispersion was obtained for 2 wt % Ru—NaY samples. But, further increase in Ru loading (3 wt % Ru loading) led to bigger Ru crystallites (6.9 nm) with low (19.3%) metal dispersion.

TABLE 1

Physicochemical property of NaY and Ru exchanged NaY catalysts.

| Entry | Catalyst | Ru/Cu metal content (%)[a] | BET surface area ($m^2/g$) | Total pore volume (cc/g) | Metal dispersion (%)[b] | Average crystallite size (nm)[b] |
|---|---|---|---|---|---|---|
| 1 | NaY | — | 886 | 0.35 | — | — |
| 2 | 1 wt % Ru—NaY | 0.97 | 861 | 0.34 | 47.4 | 2.8 |
| 3 | 2 wt % Ru—NaY | 1.98 | 851 | 0.34 | 53.2 | 2.5 |
| 4 | 3 wt % Ru—NaY | 2.95 | 827 | 0.33 | 19.3 | 6.9 |
| 5 | 2 wt % Ru—K—NaY | 1.92 | 776 | 0.30 | 48.5 | 2.7 |
| 6 | 2 wt % Ru—Rb—NaY | 1.95 | 686 | 0.27 | 45.2 | 3.0 |
| 7 | 2 wt % Ru—Cs—NaY | 1.91 | 602 | 0.23 | 41.4 | 3.2 |
| 8 | 5 wt % Cu—NaY | 4.50 | 813 | 0.31 | — | — |

[a]Chemical composition determined by ICP-OES.
[b]Determined from $H_2$ chemisorption analysis. The catalyst was reduced at 200° C. during metal dispersion experiment.

Figure 2:
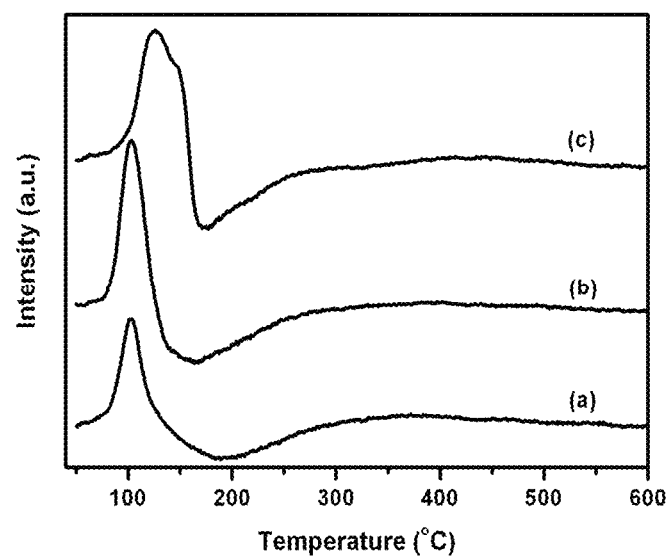
FIG. 2. $H_2$ Temperature-programmed reduction profiles of (a) 1 wt % Ru—NaY (b) 2 wt % Ru—NaY and (c) 3 wt % Ru—NaY.
Figure 3:
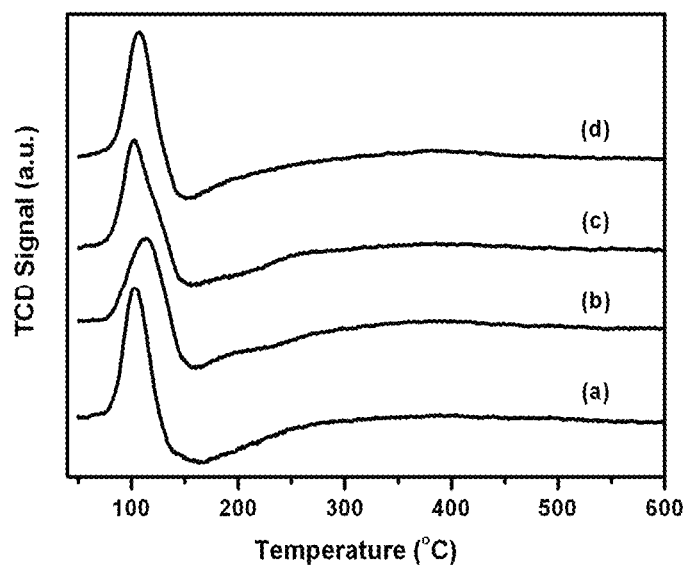
FIG. 3. $H_2$ Temperature-programmed reduction profile of a) 2 wt % Ru—NaY b) 2 wt % Ru—K—NaY c) 2 wt % Ru—Rb—NaY and d) 2 wt % Ru—Cs—NaY.

E3. Temperature Programmed Reduction:

Temperature programmed reduction (TPR) profiles of ruthenium exchanged NaY zeolite samples and alkali metal modified (K, Rb and Cs) Ru—NaY samples were evaluated and results are shown in FIG. 2 and FIG. 3, respectively. Only one broad peak in the 70-150° C. temperature regions was observed for all the samples, except for 3 wt % Ru—NaY sample. Two peaks were observed for 3 wt % Ru—NaY in the range of 80-170° C., which may be correspond to two different locations of ruthenium cations in zeolite pores/cavities.

Figure 4:
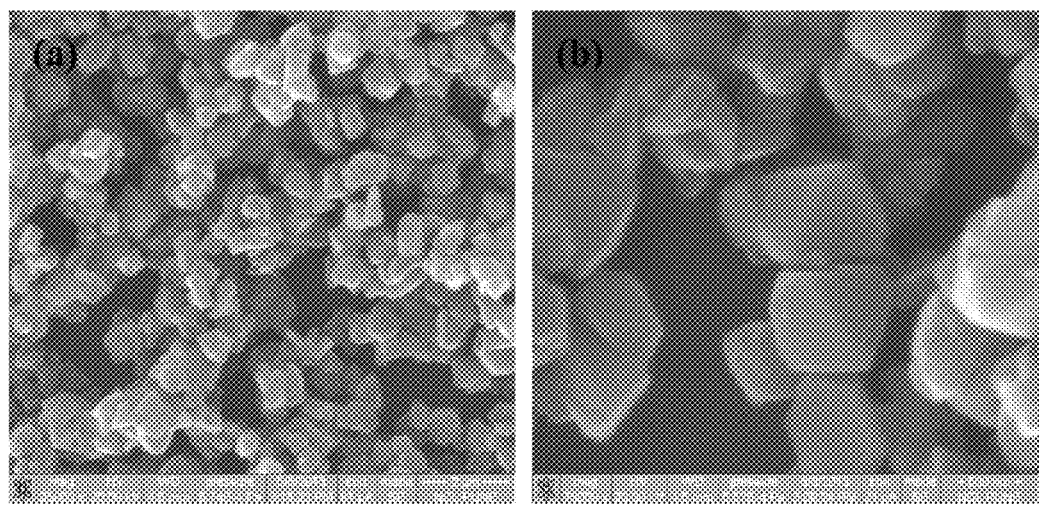
FIG. 4. SEM images of (a) NaY and (b) 0.2 wt % Ru—NaY.

E.4. Scanning Electron Microscopy (SEM):

SEM analysis of parent NaY zeolite and 2 wt % Ru—NaY sample are shown in FIG. 4. The micrograph demonstrates that the morphology of 2 wt % Ru—NaY catalyst did not change with respect to that of NaY zeolite, suggesting that no morphological transformations occurred during the ruthenium ion exchange into NaY zeolite.

Figure 5:
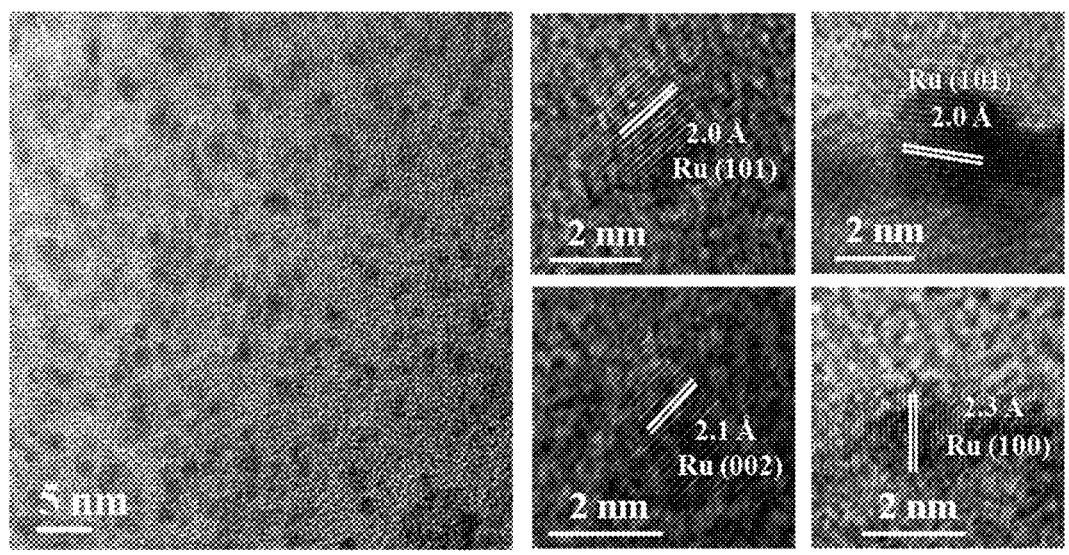
FIG. 5. TEM micrograph of 2 wt % Ru—NaY catalyst showing different Ru crystallite planes.
Figure 6:
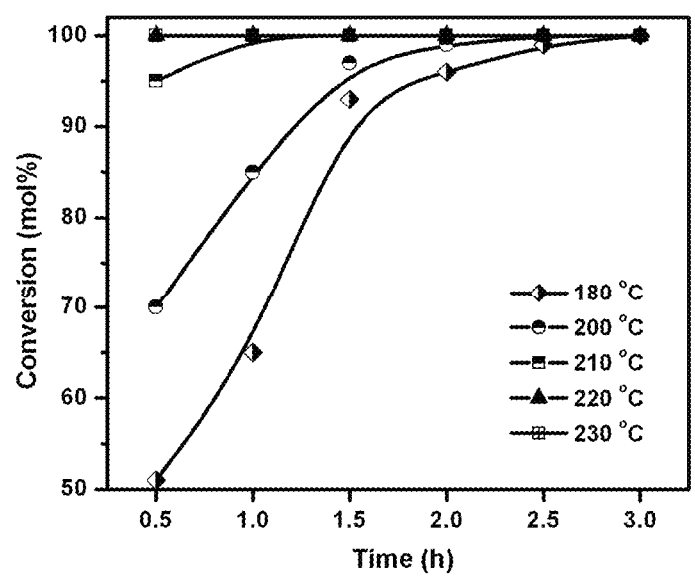
FIG. 6. Effect of reaction temperature and time on HMF conversion. Reaction conditions: HMF (1 mmol, 126 mg); catalyst (2 wt % Ru—NaY, 25 mg); $H_2$ pressure (10 bar); solvent (THF, 25 mL).
Figure 7:
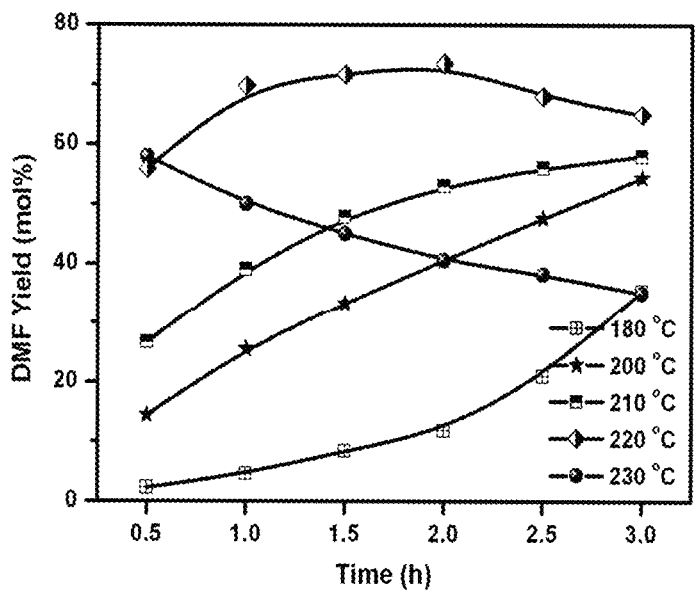
FIG. 7. Effect of reaction temperature and time on DMF yield. Reaction conditions: HMF (1 mmol, 126 mg); catalyst (2 wt % Ru—NaY, 25 mg); $H_2$ pressure (10 bar); solvent (THF, 25 mL).
Figure 8:
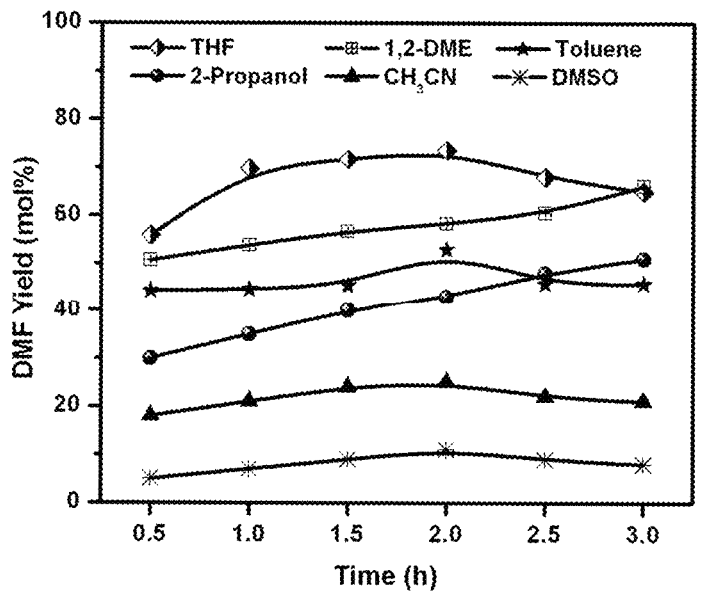
FIG. 8. Effect of solvent in liquid phase hydrogenolysis of HMF over 2 wt % Ru—NaY as a function of time. Reaction conditions: HMF (1 mmol, 126 mg); catalyst (2 wt % Ru—NaY, 25 mg); temperature (220° C.); solvent (25 mL); $H_2$ pressure (10 bar).
Figure 9:
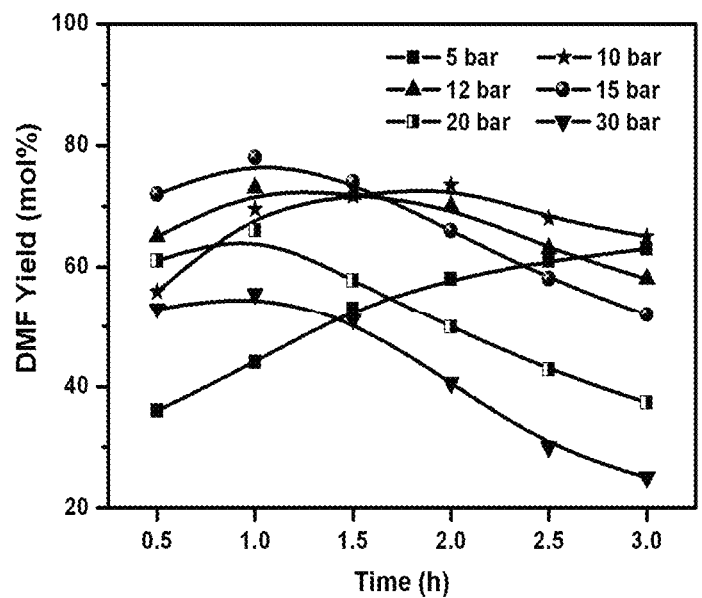
FIG. 9. Effect of hydrogen pressure on DMF yield over 2 wt % Ru—NaY as a function of time. Reaction conditions: HMF (1 mmol, 126 mg); catalyst (2 wt % Ru—NaY, 25 mg); temperature (220° C.); solvent (THF, 25 mL).
Figure 10:
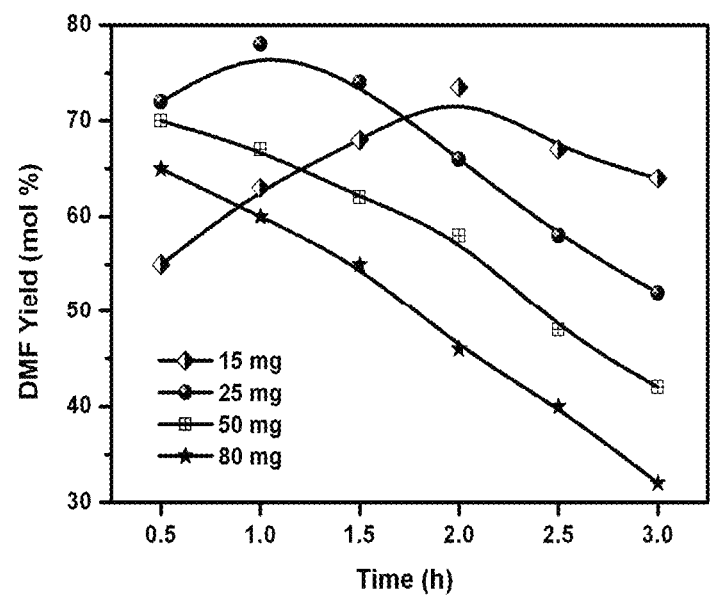
FIG. 10. Effect of catalyst content on DMF yield as a function of time. Reaction conditions: HMF (1 mmol, 126 mg); catalyst (2 wt % Ru—NaY); temperature (220° C.); $H_2$ pressure (15 bar); solvent (THF, 25 mL).
Figure 11:
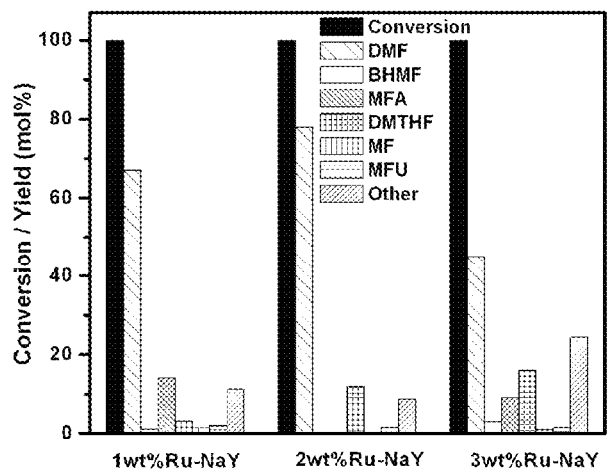
FIG. 11. Product distributions during HMF hydrogenolysis over various Ru metal containing catalysts. Reaction conditions: HMF (1 mmol, 126 mg); catalyst (25 mg); temperature (220° C.); $H_2$ pressure (15 bar); solvent (THF, 25 mL); reaction time (1 h).
Figure 12:
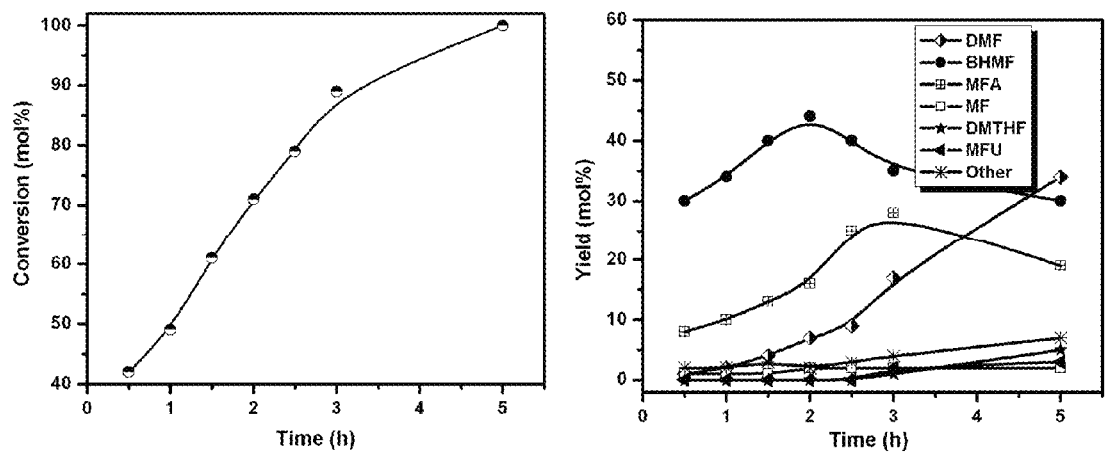
FIG. 12. HMF conversion and product yields as a function of reaction time at 170° C. Left: conversion of HMF. Right: product yields. Reaction conditions: HMF (1 mmol, 126 mg); catalyst (2 wt % Ru—NaY, 25 mg); $H_2$ pressure (10 bar); solvent (THF, 25 mL).
Figure 13:
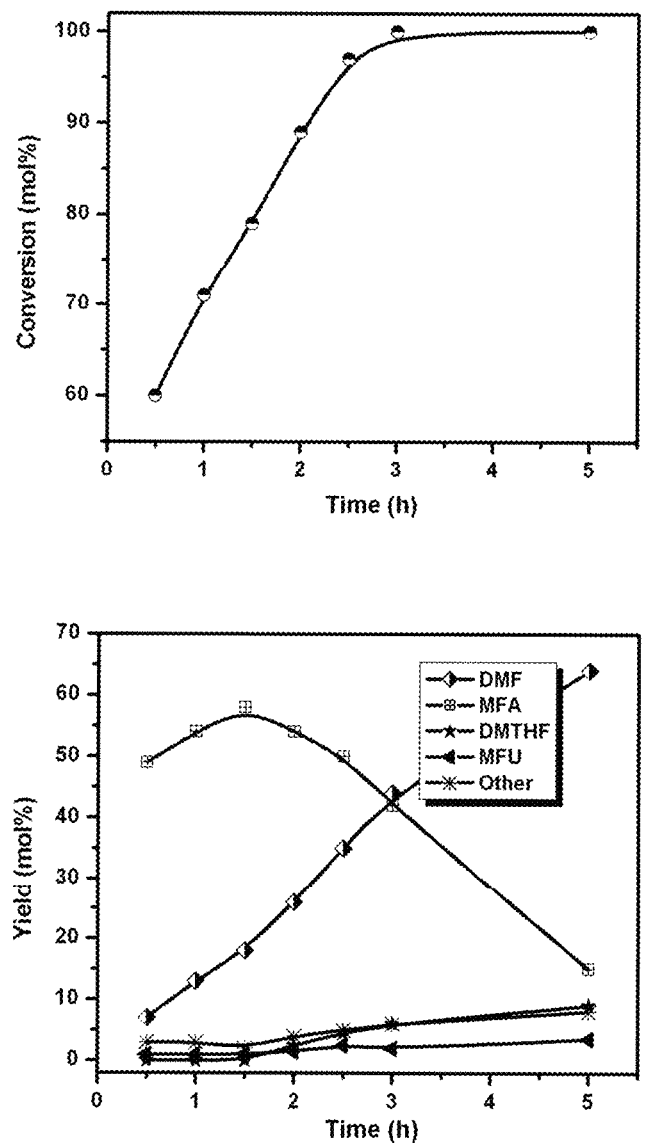
FIG. 13. MF conversion and product yields as a function of reaction time at 170° C. Left: conversion of MF. Right: product yields. Reaction conditions: MF (1 mmol, 110 mg); catalyst (2 wt % Ru—NaY, 25 mg); $H_2$ pressure (10 bar); solvent (THF, 25 mL).

E.5. Transmission Electron Microscopy (TEM):

The TEM images of 2 wt % Ru—NaY is shown in FIG. 5. Micrograph of 2 wt % Ru—NaY catalyst shows that Ru particles are well dispersed on NaY support with average crystallite size of 2 to 3 nm, which is in accordance with $H_2$ chemisorption study.

E.6. Catalytic Activity of 2 wt % Ru—NaY Catalyst for Hydrogenolysis of HMF to DMF with all Details and Yield and Selectivity The hydrogenolysis of HMF over 2 wt % Ru—NaY catalyst gave the DMF yield of 78 mol % at 100 mol % HMF conversion with DMF selectivity of 78% at optimum reaction conditions (220° C., THF, 15 bar $H_2$ and 1 h of reaction time).

Figure 14:
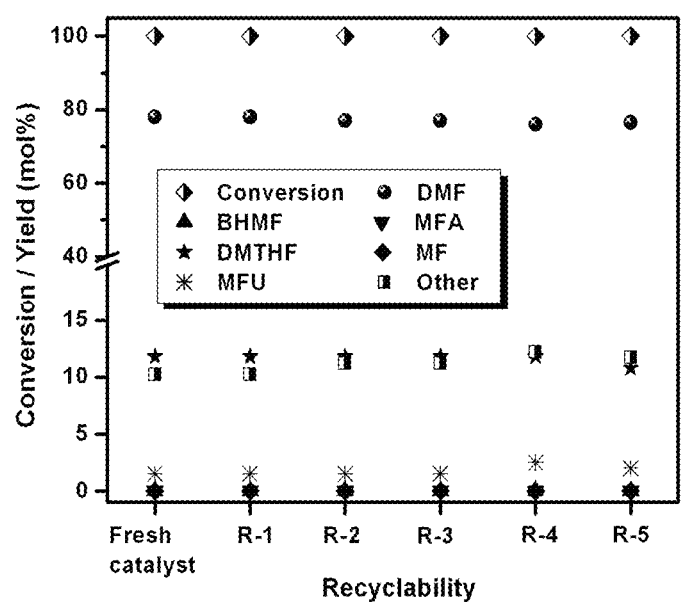
FIG. 14. The recyclability of 2 wt % Ru—NaY catalyst in hydrogenolysis of HMF. Reaction conditions: solvent (THF, 25 mL); temperature (220° C.); molar ratio of HMF to Ru (200); $H_2$ pressure (15 bar); reaction time (1 h).

E.6. Recyclability Study Over 2 wt % Ru—NaY Catalyst:

Catalyst recyclability is of great importance to use it in an industrial process. The recyclability of the 2 wt % Ru—NaY catalyst was evaluated by repeating the reaction with the same catalyst at least five times. These results are shown in FIG. 14. Results show that the catalytic performance of the 2 wt % Ru—NaY catalyst remains almost same even after being used for five times, indicating the good stability of the catalyst.

Example-2

Catalytic Activity Over 4.5 wt % Cu—NaY for Hydrogenolysis of HMF to DMF

Figure 15:
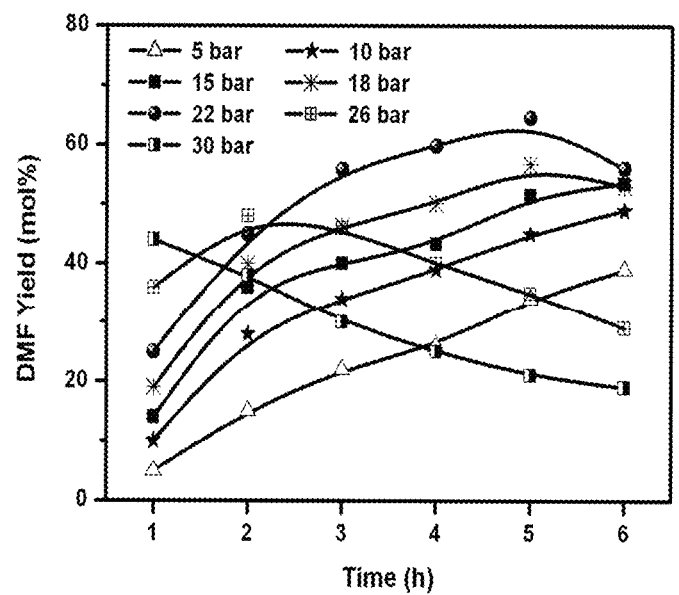
FIG. 15. Effect of hydrogen pressure on DMF yield over 4.5 wt % Cu—NaY as a function of time. Reaction conditions: HMF (1 mmol, 126 mg); catalyst (4.5 wt % Cu—NaY, 50 mg); solvent (THF, 25 mL); temperature (220° C.).

Hydrogenolysis of HMF to DMF was also studied over 4.5 wt % Cu—NaY catalyst at 220° C. by changing the hydrogen pressure from 5-30 bar, the results are shown in FIG. 15. As it can be seen from FIG. 15, DMF yield continuously increased with the time on stream at lower hydrogen pressure (5, 10, 15 and 18 bar). With further increase in pressure (22 bar), DMF yield increased with time and reaches to maximum after 5 h of reaction time, which is 64.5 mol %. However, with further increase in hydrogen pressure (26 bar), DMF yield increases up to 1 h and then decreases with the reaction time. Furthermore, when reaction was conducted again at higher hydrogen pressure (30 bar) continuous decreased in DMF yield was observed, indicating that at higher pressure ring hydrogenation of DMF was favoured leading to the formation of DMTHF. Finally, 22 bar $H_2$ pressure was found to be optimum $H_2$ pressure to achieve 64.5 mol % DMF yield at 220° C. after 5 h of reaction time.

Example-3

Catalytic Activity Over Different Noble Metal for Hydrogenolysis of HMF to DMF

All the catalysts were tested under at optimum reaction conditions obtained for of 2% Ru—NaY catalyst. Six principal products were observed: DMF, DMTHF, BHMF (2,5-bis(hydroxymethyl)furan), MF (5-methyl furfural), MFA (5-methyl furfuryl alcohol) and MFU (2-methyl furan). Other unknown products were also observed. The HMF conversion after 1 h of reaction ranged from 92 mol % for Rh—NaY to 100 mol % for Pt—NaY and Pd—NaY (Table 2). The DMF yield, the desired final product, was highest for Pd—NaY, 49.3 mol %. DMTHF, the hydrogenated compound of DMF was formed in more amount when platinum (4 mol %) and rhodium (10.7 mol %) was used as catalysts, whereas little amount of DMTHF (1.1 mol %) was observed when palladium based catalyst was used. Indicating that at the same weight loading platinum and rhodium catalysts were more active compared to the palladium catalyst for complete hydrogenation of DMF to DMTHF. Higher yield (10 mol %) of MFU was obtained for platinum based catalyst compare to rhodium and palladium as catalysts; shows that platinum catalyze both hydrogenation and carbon-carbon scission reaction. Furthermore, when platinum was used as catalyst, the majority of the HMF was converted to unidentified products. The GC chromatogram of the reaction mixture did not reveal any significant peaks, which may indicate that the undetected carbon is in the form of insoluble polymers, were formed on the catalyst surface. These insoluble polymers can be formed by the loss of formaldehyde from BHMF, followed by furfuryl alcohol polymerization.

TABLE 2

Product distribution for Hydrogenolysis of HMF over different noble metal catalysts[a].

| Entry | Catalyst | Conv. (mol %) | Yield (mol %) | | | | | | |
|---|---|---|---|---|---|---|---|---|---|
| | | | DMF | DMTHF | BHMF | MFA | MF | MFU | Other[b] |
| 1 | 2% Pt—NaY | 100 | 30.4 | 4.0 | 7.8 | 14.0 | 6.6 | 10.0 | 27.2 |
| 2 | 2% Rh—NaY | 92 | 40.1 | 10.7 | 11.5 | 12.8 | 2.6 | 2.2 | 12.1 |
| 3 | 2% Pd—NaY | 100 | 49.3 | 1.1 | 15.6 | 19.0 | 2.3 | 1.2 | 11.5 |

[a]Reaction conditions: HMF (1 mmol, 126 mg); catalyst (25 mg); temperature (220° C.); $H_2$ pressure (15 bar); solvent (THF 25 mL); reaction time (1 h).
[b]It includes MTHFA, OMBM, FA, BHMTHF and some other unidentified compounds.

Example-4

Hydrogenolysis of HMF to DMF

In a typical experiment, the reactor was charged with 1 mmol (126 mg) of HMF, solvent (25 mL), n-decane (0.2 g, internal standard) and required amount of freshly reduced catalyst. The reactor contents were mixed thoroughly and the reactor was sealed, purged 2-3 times with hydrogen and filled with 2-30 bar hydrogen pressure. Subsequently, the reaction vessel was heated under stirring at 160-250° C. for a 0.2-3 hours. Liquid samples were withdrawn periodically during the reaction and analyzed by GC (Agilent 7890A) equipped with a flame ionization detector (FID) having CP Sil 8 CB capillary column (30 m length, 0.25 mm diameter).

Example-5

Catalytic Activity Over Ru—Cu [1:3]/NaY for Hydrogenolysis of HMF to DMF

Ru—Cu [1:3]/NaY catalyst was prepared by simple ion exchanged method and tested for the selective hydrogenolysis of HMF to DMF under optimum reaction conditions obtained for 2 wt % Ru—NaY catalyst (temperature (220° C.), solvent (THF), $H_2$ pressure (15 bar)) as a function of reaction time and the results are shown in Table 3. It can be seen that DMF yield increases with the progress of reaction, suggesting that intermediates like BHMF, MFA and MF are converting to DMF with prolonged reaction time. After 2.5 h of reaction time, a maximum of 67.5 mol % DMF was obtained (Entry 5, Table 3), which decreased on further increasing reaction time. Overall, activity of Ru—Cu[1:3]/NaY catalyst for DMF formation was found to be lower when compared to 2 wt % Ru—NaY catalyst.

TABLE 3

Catalytic hydrogenolysis of HMF to DMF over Ru—Cu[1:3]/NaY catalyst[a]

| | | | Yield (mol %) | | | | | | |
|---|---|---|---|---|---|---|---|---|---|
| Entry | Time (h) | Conv. (mol %) | DMF | DMTHF | BHMF | MFA | MF | MFU | Other[b] |
| 1 | 0.5 | 92.6 | 35.5 | 1.6 | 31.9 | 11.0 | 3.2 | 1.2 | 8.2 |
| 2 | 1 | 97.1 | 47.0 | 2.3 | 17.2 | 14.3 | 3.1 | 1.2 | 12.0 |
| 3 | 1.5 | 100 | 55.0 | 3.2 | 9.8 | 15.1 | 2.2 | 1.0 | 13.7 |
| 4 | 2 | 100 | 62.3 | 4.6 | 2.6 | 9.3 | 1.5 | 2.0 | 17.7 |
| 5 | 2.5 | 100 | 67.5 | 6.4 | 0 | 4.1 | 0 | 2.4 | 19.6 |
| 6 | 3 | 100 | 59.3 | 10.5 | 0 | 0 | 0 | 4.2 | 26.0 |

[a]Reaction Conditions: HMF (1 mmol, 126 mg); catalyst (Ru—Cu [1:3]/NaY, 25 mg); solvent (THF, 25 ml); temperature (220° C.); H$_2$ pressure (15 bar).
[b]It includes MTHFA, OMBM, FA, BHMTHF, and some other unidentified compounds.

Example-6

Catalytic Hydrogenation of Furfural to Furfuryl Alcohol Over 2 wt % Ru—NaY Catalyst Furfural, which is a dehydration product of xylose can be converted to furfuryl alcohol (FFA), 2-methyl furan (MFU) and 2-methyltetrahydrofuran (MTHF). We also explored the efficiency of 2 wt % Ru—NaY catalyst for selective hydrogenation of furfural to FFA, whose results are shown in Table 4. The catalytic activity was tested by conducting the reaction in the temperature range of 150-180° C., 5-20 bar of H$_2$ pressure and with THF as solvent. It can be observed from Table 4 that temperature played significant role in furfural conversion and FFA yield. Reaction temperature of 165° C. was found to be optimum temperature to achieve 94.3% furfural conversion and 86.1% FFA yield after 8 h of reaction time (Entry 6, Table 4).

TABLE 4

Chemo-selective hydrogenation of furfural to furfuryl alcohol (FFA) with 2 wt % Ru—NaY catalyst.[a]

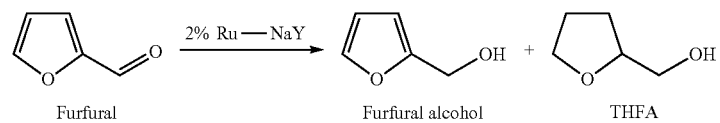

| Entry | Temp (° C.) | Time (h) | Furfural conv. (%) | FFA yield (%) | FFA selectivity (%) | THFA yield (%) | Other[e] (%) |
|---|---|---|---|---|---|---|---|
| 1[b] | 150 | 4 | 34.4 | 28.2 | 82.1 | 1.1 | 5.1 |
| 2 | 150 | 5 | 58.7 | 42.2 | 71.9 | 2.0 | 14.5 |
| 3 | 180 | 5 | 94.3 | 61.5 | 65.2 | 6.5 | 26.3 |
| 4 | 165 | 4 | 63.5 | 58.0 | 91.2 | 3.7 | 1.8 |
| 5 | 165 | 6 | 78.1 | 72.5 | 94.1 | 3.4 | 2.2 |
| 6 | 165 | 8 | 94.3 | 86.1 | 91.3 | 5.1 | 3.1 |
| 7 | 175 | 4 | 69.0 | 62.9 | 91.1 | 3.1 | 3.0 |
| 8 | 175 | 6 | 84.8 | 77.0 | 86.4 | 5.3 | 2.5 |
| 9 | 175 | 8 | 100 | 79.5 | 79.5 | 10.0 | 10.5 |
| 10[c] | 175 | 6 | 100 | 46.7 | 46.7 | 24.1 | 29.2 |
| 11[d] | 175 | 6 | 100 | 5.8 | 5.8 | 53.5 | 40.7 |

[a]Reaction conditions: furfural (4 mmol, 0.384 g); catalyst (2 wt % Ru—NaY, 30 mg); H$_2$ pressure (10 bar); solvent (THF, 25 mL);
[b]5 bar;
[c]15 bar and
[d]20 bar.
[e]Includes MFU, furan, THF and MTHF.

ADVANTAGES OF INVENTION a. DMF is a good alternative to bio-ethanol. DMF has superior properties compared to ethanol.
b. A catalyst that is highly efficient and economical in terms of DMF yield.
c. The catalyst is re-usable and very easy to prepare, store and use in the application.
d. The $H_2$ pressures and temperatures used in the process are moderate and do not need any expensive equipment for carrying out the process.

We claim:

1. An improved process for the preparation of compound of formula 1 wherein the said process comprising reaction of compound of formula 2 in presence of ruthenium catalyst at 160-250° C. for 0.2-3 hours under hydrogen pressure in the range of 2-30 bar in a solvent wherein improvement is characterized in using ruthenium catalyst which comprises ruthenium nanoparticles in combination with transition metal supported on NaY zeolite

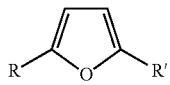

formula 1 wherein,
R=$CH_3$ or H
R'=$CH_3$ or $CH_2OH$

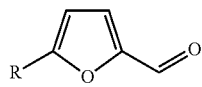

formula 2 wherein,
R=$CH_2OH$ or H.

2. The process as claimed in claim 1, wherein transition metals are selected from the group consisting of Cu, Ni, Re, Cr, Mn, Fe and Co in the range of 1-10 wt % of the catalyst.

3. The process as claimed in claim 1, wherein ruthenium catalyst supported on NaY zeolite is selected from 2% Ru—NaY, 2% Ru—K—NaY, 2% Ru—Rb—NaY, 2% Ru—Cs—NaY, 2% Ru—Mg—NaY, 2% Ru—Ca—NaY, 2% Ru—Sr—NaY, 2% Ru—Ba—NaY, Ru—Cu [1:3]/NaY.

4. The process as claimed in claim 1, wherein the solvent is tetrahydrofuran.

5. The process as claimed in claim 1, wherein compound of formula 1 is selected from the group consisting of 2,5-dimethylfuran and furfuryl alcohol.

6. The process as claimed in claim 1, wherein compound of formula 2 is selected from the group consisting of 5-hydroxymethylfurfural and furfural.

7. The process as claimed in claim 1, wherein mole ratio of 5-hydroxymethylfurfural and ruthenium catalyst is in the range of 150-250.

8. The process as claimed in claim 1, wherein conversion of compound of formula 2 is in the range of 90-100 mol %.

9. The process as claimed in claim 1, wherein yield of compound of formula 1 is in the range of 75-90 mol %.

\* \* \* \* \*